(12) United States Patent
Cheng et al.

(10) Patent No.: US 10,632,136 B2
(45) Date of Patent: Apr. 28, 2020

(54) SOLUBLE DIETARY FIBER AND PREPARATION METHOD THEREOF

(71) Applicant: SHANDONG LONGLIVE BIO-TECHNOLOGY CO., LTD, Dezhou, Shandong (CN)

(72) Inventors: Shaobo Cheng, Shandong (CN); Lin Xiao, Shandong (CN); Shulin Qin, Shandong (CN); Ruirui Xia, Shandong (CN); Xianfu Liu, Shandong (CN); Jinlong Yan, Shandong (CN); Ying Li, Shandong (CN); Lingjun Kong, Shandong (CN); Yan Wang, Shandong (CN); Zhiguang Zou, Shandong (CN); Chengquan Zhang, Shandong (CN)

(73) Assignee: SHANDONG LONGLIVE BIO-TECHNOLOGY CO., LTD, Dezhou, Shandong (CN)

(*) Notice: Subject to any disclaimer, the term of this patent is extended or adjusted under 35 U.S.C. 154(b) by 0 days.

(21) Appl. No.: 15/777,665

(22) PCT Filed: Aug. 25, 2016

(86) PCT No.: PCT/CN2016/096735
§ 371 (c)(1),
(2) Date: May 20, 2018

(87) PCT Pub. No.: WO2017/107527
PCT Pub. Date: Jun. 29, 2017

(65) Prior Publication Data
US 2018/0296581 A1 Oct. 18, 2018

(30) Foreign Application Priority Data
Dec. 25, 2015 (CN) .......................... 2015 1 0999427

(51) Int. Cl.
| | | |
|---|---|---|
| *A61K 31/702* | (2006.01) |
| *C13K 13/00* | (2006.01) |
| *A23L 33/21* | (2016.01) |
| *C12P 19/00* | (2006.01) |
| *A23L 33/24* | (2016.01) |
| *A61K 31/715* | (2006.01) |
| *C12P 19/04* | (2006.01) |

(52) U.S. Cl.
CPC ............ *A61K 31/702* (2013.01); *A23L 33/21* (2016.08); *A23L 33/24* (2016.08); *A61K 31/715* (2013.01); *C12P 19/00* (2013.01); *C12P 19/04* (2013.01); *C13K 13/00* (2013.01); *C13K 13/002* (2013.01); *A23V 2002/00* (2013.01)

(58) Field of Classification Search
CPC ........ A23L 33/24; A23L 33/21; A61K 31/702
See application file for complete search history.

(56) References Cited

U.S. PATENT DOCUMENTS

| | | | |
|---|---|---|---|
| 5,658,765 A | 8/1997 | Noguchi et al. |
| 5,939,309 A | 8/1999 | Suwa |
| 2009/0062232 A1 | 3/2009 | Fujikawa et al. |

FOREIGN PATENT DOCUMENTS

| | | | | |
|---|---|---|---|---|
| CN | 1333371 A | 1/2002 | |
| CN | 1333371 | * 7/2002 | ............... C12N 9/24 |
| CN | 1796656 A | 7/2006 | |
| CN | 1840674 A | 10/2006 | |
| CN | 102399842 A | 4/2012 | |
| CN | 102978297 | * 3/2013 | ............. C13K 13/00 |
| CN | 102978297 A | 3/2013 | |
| CN | 104593446 A | 5/2015 | |
| EP | 0265970 A2 | 5/1988 | |
| JP | S52066641 | 6/1977 | |
| JP | S63112979 A | 5/1988 | |
| JP | H04309501 A | 11/1992 | |
| JP | H09248153 A | 9/1997 | |
| JP | 2006296224 A | 11/2006 | |
| JP | 2012157350 A | 8/2012 | |

OTHER PUBLICATIONS

Applied Carbohydrate Science 2012, vol. 2 No. 3 p. 165-168.
The First Office Action dated Jun. 11, 2019 for Japanese patent application No. 2018-532714.
International Search Report for PCT/CN2016/096735 dated Nov. 21, 2016, ISA/CN.
Carvalho Ana Flavia Azevedo et al: "Xylo-oligosaccharides from lignocellulosic materials: Chemical structure, health benefits and production by chemical and enzymatic hydrolysis", Food Research International, Elsevier, Amsterdam, NL, vol. 51, No. 1, Nov. 29, 2012, pp. 75-85, XP028995415.
Appukuttan Aachary A et al:"Xylooligosaccharides (XOS) as an emerging prebiotic: microbial synthesis, utilization, structural characterization, bioactive properties, and applications.", Comprehensive Reviews in Food Science and Food Safety, vol. 10, No. 1, Jan. 2011, pp. 2-16, XP002793108.
Search Report dated Aug. 9, 2019 for European patent application No. 16877339.8.

* cited by examiner

*Primary Examiner* — Pancham Bakshi
(74) *Attorney, Agent, or Firm* — Yue (Robert) Xu; Apex Attorneys at Law, LLP

(57) ABSTRACT

A soluble dietary fiber having a xylooligosaccharide purity of 70% or greater. The xylooligosaccharide has a total xylobiose and xylotriose content of 45% or great. The soluble dietary fiber has a higher content of an effective component, thus improving the proliferation of a *Bifidobacterium* and *Lactobacillus*, and significantly reducing blood glucose.

3 Claims, 7 Drawing Sheets

SOLUBLE DIETARY FIBER AND PREPARATION METHOD THEREOF

CROSS REFERENCE TO RELATED APPLICATIONS

This is a US National Phase application based upon PCT Application No. PCT/CN2016/096735, filed Aug. 25, 2016 and titled "SOLUBLE DIETARY FIBER AND PREPARATION METHOD THEREOF", which claims priority to Chinese Patent Application No. 201510999427.1, filed Dec. 25, 2015, the disclosures of which are hereby incorporated by reference in their entirety.

FIELD

The present invention relates to the field of food technology, particularly to a soluble dietary fiber and a preparation method thereof.

BACKGROUND

Soluble dietary fiber is a type of dietary fiber that can be dissolved in hot or warm water, can be degraded by various microorganisms in the intestine without being decomposed by human digestive enzymes. Soluble dietary fiber can maintain intestinal health, strengthen immunity, reduce blood sugar, blood lipids and blood pressure, reduce the incidence of diabetes, reduce cholesterol, prevent cardiovascular disease, and also has other physiological functions.

Xylooligosaccharide, also known as xylo-oligomer, is a type of soluble dietary fiber that can be dissolved not only in warm or hot water, but also in cold water or ethanol solvent. It is mainly composed of 2-9 xylose molecules bound with beta-1,4 glycosidic bonds to form a functional polymer sugar, in which xylobiose, xylotriose, and xylotetraose are the main active ingredients. Xylooligosaccharide cannot be decomposed by various digestive fluids of the human body, the function of which is to not raise blood sugar, but reduce cholesterol, bidirectionally regulate constipation and diarrhea, etc. At the same time, it is contributive to the intestinal function protection, improvement of the intestinal flora balance in the body (human and animal), promotion of the growth of intestinal beneficial bacteria and inhibition of the propagation of harmful microorganisms, it can significantly improve the proportion of *Bifidobacterium* and other probiotics, and thus promotes the absorption of nutrient minerals, and improves body immunity. Therefore, as a functional sweetener and additive, xylooligosaccharide can meet all the population, including special populations with diabetes, obesity, etc.

However, at present in different fields of applications, food grade xylooligosaccharide still faces many problems. First, the purity, color and luster, impurities and other indicators directly affect the appearance quality of the product. Second, the relatively low proportion of functional active ingredients (xylobiose, xylotriose) in the product affects the health benefit of the product.

SUMMARY OF THE INVENTION

The technical problem to be solved by the disclosure is to provide a soluble dietary fiber and a preparation method thereof. The soluble dietary fiber product obtained has the characteristics of high xylooligosaccharide purity, good color and luster, fewer impurities, as well as high proportion of active ingredients (xylobiose, xylotriose).

The present disclosure provides a soluble dietary fiber, the purity of xylooligosaccharide is 70% or more, and in the xylooligosaccharide, the total content of xylobiose and xylotriose is 45% or more.

Preferably, after hydrolysis of the xylooligosaccharide, the monosaccharide components comprise:

xylose 70 wt % to 86 wt %, and arabinose 2 wt % to 15 wt %.

Preferably, the purity of xylooligosaccharide is 80% or more; and in the xylooligosaccharide, the total content of xylobiose and xylotriose is 55% or more.

Preferably, after hydrolysis of the xylooligosaccharide, the monosaccharide component comprises:

xylose 82 wt % to 88 wt %, and arabinose 1 wt % to 12 wt %.

Preferably, the purity of xylooligosaccharide is 90% or more; and in the xylooligosaccharide, the total content of xylobiose and xylotriose is 50% or more.

Preferably, after hydrolysis of the xylooligosaccharide, the monosaccharide component comprises:

xylose 83 wt % to 99 wt %, and arabinose 1 wt % to 5 wt %.

Preferably, the soluble dietary fiber is a xylooligosaccharide syrup or xylooligosaccharide powdered sugar.

The present disclosure also provides a preparation method for the soluble dietary fiber, which comprises:

(A) subjecting lignocelluloses to continuous countercurrent leaching and separation to obtain a solid material;

(B) subjecting the solid material obtained in step (A) to continuous steaming processing in a transverse pipe to obtain a steamed material;

(C) subjecting the steamed material obtained in step (B) to enzymolysis by xylanase to obtain a soluble dietary fiber crude sugar liquor;

(D) subjecting the crude sugar liquor obtained in step (C) to decolorization, desalination and filtration to obtain a soluble dietary fiber sugar liquor;

(E) concentrating or drying, to obtain a soluble dietary fiber I;

in the soluble dietary fiber I, the purity of xylooligosaccharides is 80% or more.

Preferably, after step (E), the method further comprises:

(F) subjecting the soluble dietary fiber I prepared in step (E) to chromatographic separation to obtain a soluble dietary fiber II and raffinate;

in the soluble dietary fiber II, the purity of xylooligosaccharide is 90% or more.

Preferably, after step (F), the method further comprises:

(G) compounding the raffinate obtained in step (F) with the soluble dietary fiber sugar liquor obtained in step (D) to obtain a soluble dietary fiber III;

in the soluble dietary fiber III, the purity of xylooligosaccharide is 70% or more.

Compared with the prior art, the present disclosure provides a soluble dietary fiber, wherein the purity of xylooligosaccharides is 70% or more; and in the xylooligosaccharides, the total content of xylobiose and xylotriose is 45% or more. The soluble dietary fiber provided by the present disclosure has higher content of effective component, has better effect of proliferation on *Bifidobacterium* and *Lactobacillus*, and can reduce blood sugar obviously.

The present disclosure also provides a preparation method of a soluble dietary fiber, which comprises: (A) subjecting lignocelluloses to continuous countercurrent leaching and separation to obtain a solid material; (B) subjecting the solid material obtained in step (A) to continuous steaming processing in a transverse pipe to obtain a steamed material; (C)

subjecting the steamed material obtained in step (B) to enzymolysis by xylanase to obtain a soluble dietary fiber crude sugar liquor; (D) subjecting the crude sugar liquor obtained in step (C) to decolorization, desalination and filtration to obtain a soluble dietary fiber sugar liquor; and (E) concentrating or drying to obtain a soluble dietary fiber I; in the soluble dietary fiber I, the purity of xylooligosaccharides is 80% or more. The present disclosure applies continuous countercurrent leaching technology and continuous steaming technology processing in a transverse pipe to the extraction process of xylooligosaccharide, effectively reduces the binding force between hemicellulose macromolecules in raw materials, the hemicelluloses are free from lignocellulosic component. The free hemicelluloses are more conducive to the combination with xylanase, improves the enzymolysis efficiency with xylanase and reduces the amount of xylanase used compared with the traditional process. At the same time using xylanase purification process, it achieves that the xylanase is mainly endo-type, further degradation of xylooligosaccharide to xylose by exo-xylanase such as xylosidase and the like is avoided, the total yield of xylooligosaccharides is improved, and the disadvantage of degrading of cellulose components by cellulose and producing cellobiose are avoided at the same time; and by screening appropriate xylanase, the composition of the functional components in the water-soluble dietary fiber is optimized, the proportion of the active ingredient mainly composed of xylobiose and xylotriose is improved.

DETAILED DESCRIPTION OF THE INVENTION

Figure 1:
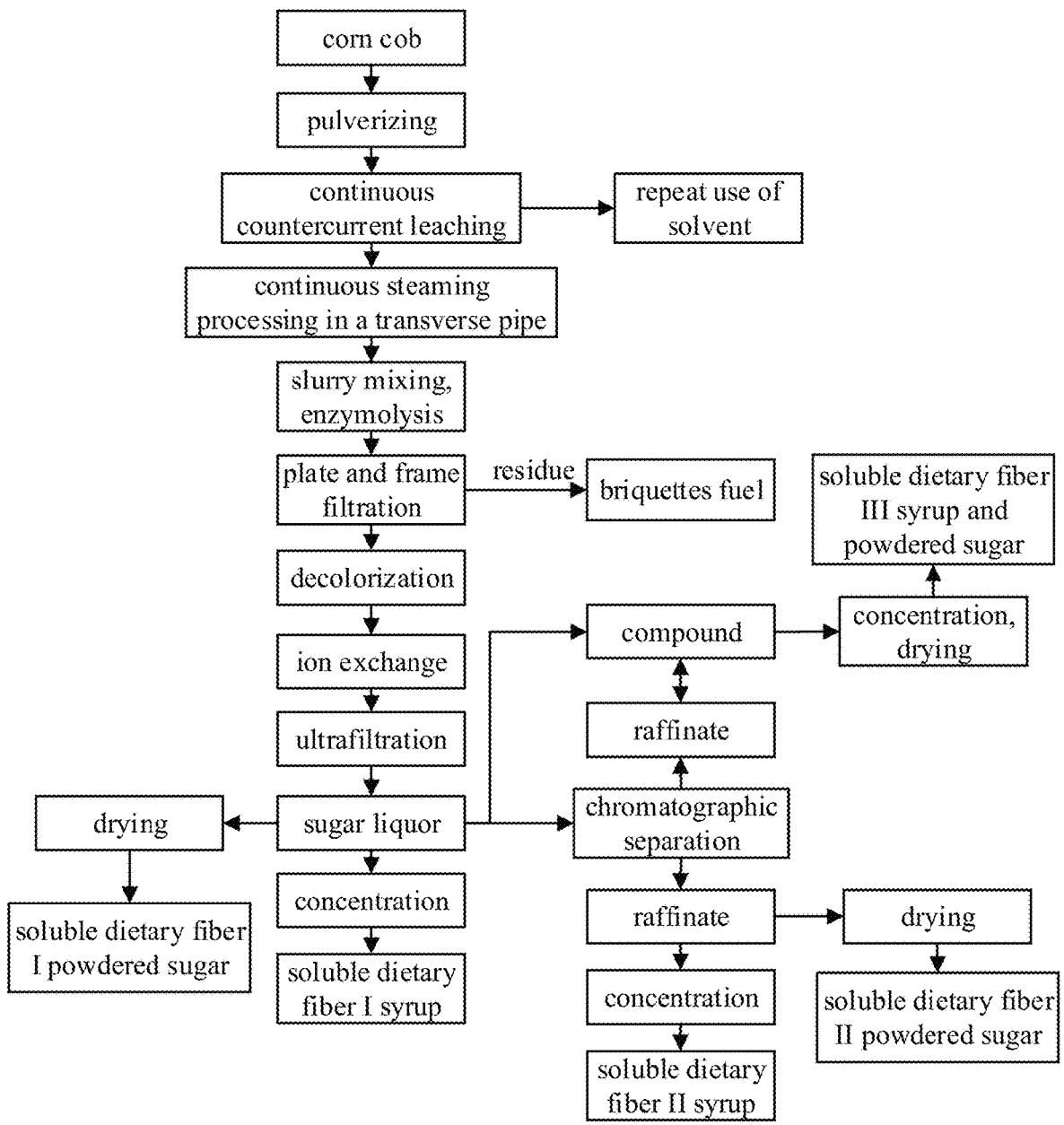
FIG. 1 is a flow chart of Example 1 of the present disclosure.

The present disclosure provides a soluble dietary fiber, wherein the purity of xylooligosaccharide is 70% or more, and in the xylooligosaccharide, the total content of xylobiose and xylotriose is 45% or more.

The soluble dietary fiber provided by the present disclosure has a higher content of effective component, has better effect of proliferation on *Bifidobacterium* and *Lactobacillus*, and can reduce blood glucose obviously.

In the present disclosure, the purity of the xylooligosaccharides means mass percent of content of xylooligosaccharides in total sugar content.

The soluble dietary fiber provided by the present disclosure comprises xylooligosaccharide, wherein the xylooligosaccharide is a powdered sugar or syrup.

Preferably, the purity of the xylooligosaccharide is 70% or more; and in the xylooligosaccharide, the total content of xylobiose and xylotriose is 45% or more.

When the xylooligosaccharide is a syrup, the syrup is a yellow or light yellow viscous transparent liquid, and solid content (mass concentration of sugar) is 70% or more. When the xylooligosaccharide is a powdered sugar, the powdered sugar is a white or slightly yellow powder. The components are:

xylobiose at a preferred mass percent is of 25% to 60%, more preferably 25% to 28%; xylotriose at a preferred mass percent is of 20% to 30%, more preferably 20% to 22%; and xylotetraose at a preferred mass percent is of 5% to 20%, more preferably 11% to 13%.

After hydrolysis of the xylooligosaccharide, the component comprises, but is not limited to: xylose 70 wt % to 86 wt %, and arabinose 2 wt % to 15 wt %.

In some specific embodiments of the present disclosure, the purity of the xylooligosaccharide is 80% or more; and in the xylooligosaccharide, the total content of xylobiose and xylotriose is 55% or more. Preferably, the mass percent of xylobiose is 30% to 60%, the mass percent of xylotriose is 25% to 40%, and the mass percentt of xylotetraose is 10% to 30%.

After hydrolysis of the xylooligosaccharides, the component comprises, but is not limited to: xylose 82 wt % to 88 wt %; and arabinose 1 wt % to 12 wt %, preferably 4 wt % to 10 wt %.

The xylooligosaccharide is a powdered sugar or syrup. The syrup is a yellow or light yellow viscous transparent liquid with a solid content (mass concentration of the sugar) of 70% or more; the powdered sugar is a white or slightly yellow powder.

In other embodiments of the present disclosure, the purity of the xylooligosaccharide is 90% or more; and in the xylooligosaccharide, the total content of xylobiose and xylotriose is 50% or more. Preferably, the mass percent of xylobiose is 25% to 60%, more preferably 27% to 33%; the mass percent of xylotriose is 25% to 40%, more preferably 29% to 31%; and the mass percentt of xylotetraose is 10% to 30%, more preferably 16% to 19%.

After hydrolysis of the xylooligosaccharides, the component comprises, but is not limited to; xylose 83 wt % to 99 wt %, preferably 84% to 90%; and arabinose 1 wt % to 5 wt %, preferably 2 wt % to 4 wt %.

The xylooligosaccharide is a powdered sugar or syrup. The syrup is a yellow or light yellow viscous transparent liquid with a solid content (mass concentration of the sugar) of 70% or more; the powdered sugar is a white or slightly yellow powder.

The present disclosure does not particularly limit the hydrolysis method of the xylooligosaccharide, it may be a hydrolysis method well known to those skilled in the art. The acid hydrolysis method is preferably adopted in the present disclosure.

After hydrolysis, the content of each monosaccharide component is isolated and quantitatively determined by high performance liquid chromatography.

The present disclosure also provides a preparation method of a soluble dietary fiber, which comprises:

(A) subjecting lignocelluloses to continuous countercurrent leaching and separation to obtain a solid material;

(B) subjecting the solid material obtained in step (A) to continuous steaming processing in a transverse pipe to obtain a steamed material;

(C) subjecting the steamed material obtained in step (B) to enzymolysis by xylanase to obtain a soluble dietary fiber crude sugar liquor;

(D) subjecting the crude sugar liquor obtained in step (C) to decolorization, desalination and filtration to obtain a soluble dietary fiber sugar liquor;

(E) concentrating or drying to obtain a soluble dietary fiber I;

in the soluble dietary fiber I, the purity of xylooligosaccharides is 80% or more. The component of the xylooligosaccharide is the same as that of the above-mentioned xylooligosaccharide having a purity of 80% or more, and will not be repeated here.

The present disclosure uses the lignocellulose rich in hemicellulose as raw material. The lignocellulose may be a lignocellulose well known in the art, preferably any one or more of corncob, cottonseed hull, rice husk and straw, more preferably corncob and/or cottonseed hull.

First, lignocelluloses are subjected to continuous countercurrent leaching. Preferably, specific operation of the continuous countercurrent leaching is: the lignocellulose raw material is pulverized into particles having a length or particle size of 0.1 cm to 5 cm, placed in a continuous countercurrent extractor, a solvent medium(s) is added in such an amount that the ratio of the raw material to the solvent medium is 1 g:(4-10) mL, the controlled temperature is 30° C. to 90° C., the extraction time is 20 to 60 minutes. Then the solid material and the leach liquor which is rich in monosaccharides are separated by continuous solid-liquid separations. The leach liquor can be recycled for reuse.

In the present disclosure, the solvent medium is water, an acid solution, an alkali solution or an organic solvent. The acid solution is preferably any one or more of sulfuric acid, hydrochloric acid, formic acid and acetic acid; the alkali solution is preferably a aqueous solution formulated with any one or more of sodium hydroxide, potassium hydroxide, ammonia solution or sodium bicarbonate; the organic solvent is preferably ethanol and/or ethyl acetate.

The present disclosure adopts continuous countercurrent leaching technology, removes soluble miscellaneous sugars from the side chain of raw material xylan, reduces the content of monosaccharides such as glucose and xylose in the product, and improves the purity of the soluble dietary fiber product.

After the solid material is obtained, the solid material obtained by the above-mentioned process is subjected by the present disclosure to continuous steaming processing in a transverse pipe, a steamed material is obtained.

Specifically, the continuous steaming processing in a transverse pipe is: the solid material is pushed into a transverse pipe through a screw conveyor, a material plug is formed, steam is introduced, they are thoroughly mixed and steamed under the tumbling action of the screw conveying and the steam to efficiently dissolve the hemicellulose form the raw material; the steaming pressure is preferably 0.2 to 1.0 MPa, and the steaming time is preferably 10 to 90 minutes.

The present disclosure adopts continuous steaming processing in a transverse pipe, reduces the dissolution rate of monosaccharide, improves the dissolution rate of hemicellulose xylan, reduces the amount of xylanase used, and at the same time improves the composition of the steaming solution, increases the proportion of xylobiose and xylotriose in the product.

After the steamed material is obtained by continuous steaming processing in a transverse pipe, the material is subjected to enzymolysis by xylanase, a soluble dietary fiber crude sugar liquor is obtained. Specifically, the steamed material is subjected to pressure relief and is sprayed into an enzymolysis tank, water is added to the enzymolysis tank, the mass ratio of material to water is adjusted to 1:(4-16), and the pH is adjusted to 3.5-6.5. Xylanase is added for enzymolysis in an amount of $1 \times 10^4$ U to $8 \times 10^4$ U of xylanase per kilogram of dry matter, enzymolysis reaction is carried on, a soluble dietary fiber crude sugar liquor is prepared.

In the present disclosure, the xylanase may be a xylanase prepared by fermentation with a microbial strain or an endo-xylanase commercially available. In the present disclosure, the xylanase is preferably a xylanase prepared by fermentation with *Trichoderma reesei* strain and purification. The *Trichoderma reesei* strain is numbered CICC 13052.

Specifically, the method preferred by this disclosure for the preparation of xylanase by fermentation with *Trichoderma reesei* strain and purification is: 2 wt % to 6 wt % of corncob (20 to 80 mesh), 0.25 wt % to 0.5 wt % of xylooligosaccharide; 0.25 wt % to 1 wt % of yeast extract; 0.25 wt % to 1 wt % of peptone; 0.25 wt % to 0.5 wt % of yeast powder; 0.02 wt % to 0.06 wt % of $KH_2PO_4$; 0.02 wt % to 0.05 wt % of $MgSO_4.7H_2O$; 0.01 wt % of $FeSO_4$, initial pH 6.0, an enzyme-producing medium is prepared; the strain is inoculated in the enzyme-producing medium, 28° C. to 32° C., fermented for 64 h to 84 h, the culture is filtrated through a plate and frame filter, the solid is separated from the liquid, an xylanase crude enzyme solution is obtained. The crude enzyme solution is concentrated 10-fold to 50-fold by ultrafiltration, and separated with gel filtration chromatography (Sephdex G-75), 20000-90000 Da protein with endo-xylanase activity is collected.

In the present disclosure, the temperature of the enzymolysis reaction is preferably 40° C. to 80° C., and the reaction time is preferably 4 h to 20 h. In the present disclosure, preferably after the completion of the enzymolysis reaction, the system is heated to 80° C. to 100° C., the heat is preserved for 10 to 60 minutes, the xylanase is inactivated, and filtrated through a belt dryer or a rotary vacuum drum.

The present disclosure applies continuous countercurrent leaching technology and continuous steaming technology processing in a transverse pipe to the extraction process of the soluble dietary fiber, effectively reduces the binding force between the hemicellulose macromolecules in raw materials, such that the hemicelluloses are free from the lignocellulosic component. This kind of free hemicelluloses is more conducive to enzymolysis, compared with the traditional process, the enzymolysis efficiency with xylanase is improved and the amount of xylanase used is reduced. At the same time using xylanase purification process, it achieves that xylanase is mainly endo-type, further degradation of xylooligosaccharide to xylose by exo-xylanase such as xylosidase and the like is avoided, the total yield of xylooligosaccharides is improved, and the disadvantage of degradation of cellulose components into cellobiose by cellulase is avoid at the same time; and by screening appropriate xylanase, the composition of the functional components in the water-soluble dietary fiber is optimized, the proportion of the active ingredient mainly composed of xylobiose and xylotriose is improved.

After the soluble dietary fiber crude sugar liquor is obtained, it is subjected to decolorization, desalination and filtration, a soluble dietary fiber sugar liquor is obtained.

The present disclosure does not particularly limit the methods of decolorization, desalination and filtration, it may be a method known to those skilled in the art.

In the present disclosure, it is preferable that the decolorization method is a decolorization with activated carbon, and the activated carbon is preferably a food grade activated carbon. The added amount of the activated carbon is preferably 0.1% to 2% by weight of the crude sugar liquor, the decolorization temperature is preferably 60° C. to 100° C., and the decolorization time is preferably 10 to 60 minutes. After the decolorization, a solid-liquid separation is carried out to obtain a decolorized crude sugar liquor.

The desalination method is ion exchange desalination. Specifically, the decolorized crude sugar liquor is desalinated through cation-anion-cation exchange resins, in such a flow rate that the amount of the crude sugar flowed per hour is preferably 1 to 5 times the volume of the resin.

The filter is ultrafiltration. The pore size of the ultrafiltration membrane is preferably 3000 Da to 6000 Da, and after the macromolecule saccharide is removed by the ultrafiltration, a soluble dietary fiber sugar liquor can be obtained.

The sugar liquor is concentrated or dried, a soluble dietary fiber I can be obtained; in the soluble dietary fiber I, the purity of xylooligosaccharides is 80% or more.

Specifically, the soluble dietary fiber I obtained by concentration of the sugar liquor is a xylooligosaccharide syrup. The present disclosure does not particularly limit the concentration method, it may be a concentration method known to those skilled in the art. Preferably, the concentration is a concentration with a triple effect evaporator, the temperature of the first effect is preferably 80° C. to 90° C., the temperature of the second effect is preferably 70° C. to 80° C., and the temperature of the third effect is preferably 60° C. to 70° C.

The soluble dietary fiber I obtained by drying the sugar liquor is a xylooligosaccharide powdered sugar. The present disclosure does not particularly limit the drying method, it may be a drying method known to those skilled in the art. In the present disclosure, the drying is preferably vacuum belt drying, vacuum rake drying or spray drying.

The parameters of the vacuum belt drying preferred by the present disclosure are as follows: the vacuum belt dryer has three heating evaporation zones in which the temperature of the first section is 90° C. to 115° C., the heating temperature of the second section is 100° C. to 115° C., the heating temperature of the third section is 80° C. to 100° C., the cooling zone temperature is 10° C. to 35° C., the vacuum is −0.08 MPa to −0.098 MPa, and the coating thickness is 0.3 cm to 1 cm.

The parameters of the vacuum rake drying are: the heating temperature is 80° C. to 100° C., the vacuum degree is −0.04 MPa to −0.096 MPa, and the rake tooth speed is 6 rpm to 12 rpm.

The parameters of the spray drying are: the hot air inlet temperature is 100° C. to 180° C., the outlet temperature is 65° C. to 130° C.

After the soluble dietary fiber I is obtained by the above-mentioned method, preferably the method further comprises step (F):

subjecting the above-mentioned prepared soluble dietary fiber I to chromatographic separation, a soluble dietary fiber II and raffinate are obtained.

The chromatographic separation of the present disclosure is preferably carried out by means of a simulated moving bed chromatographic separation system. The preferred system pressure is 0.8 MPa to 1.1 MPa and the mass fraction of the feedstock sugar liquor is 40% to 60%.

In the soluble dietary fiber II, the purity of xylooligosaccharide is 90% or more. The xylooligosaccharides have the same components as the above-mentioned xylooligosaccharides having the purity of 90% or more, and will not be repeated here.

In the present invention, the soluble dietary fiber II may also be concentrated and a syrup is obtained, or be dried and a powdered sugar is obtained. The method of concentration or drying is the same as above and will not be repeated here.

The component of the raffinate is: xylooligosaccharide (xylobiose-xyloheptaose) 8% to 30%, glucose 5% to 15%, xylose 40% to 60%, and arabinose 20% to 40%. In the present disclosure, it has been found that the raffinate is rich in arabinose. Arabinose has the effect of inhibiting the metabolism and absorption of sucrose, can selectively has noncompetitive inhibition effect(s) on the activity of sucrase in the intestinal tract, such that the absorption of sucrose by the intestinal tract obviously reduced, also the blood glucose level is reduced therefore. In addition, the arabinose can noncompetitively inhibit the disaccharidase such as sucrase which exist on the surface of the microvilli (mucosal villi border) of the small intestinal mucosa, and as a result, the decomposition of carbohydrates into glucose or fructose is slowed down, and the absorption is reduced. Therefore, at the same time that the conversion of sugar into fat is inhibited, the sharp increase in blood glucose levels after eating (hyperglycemia) is also inhibited, and satiety is sustained, appetite is inhibited and weight loss is achieved.

Therefore, it is preferred in the present disclosure that after the soluble dietary fiber II and raffinate are obtained, the method further includes step (G):

compounding the obtained raffinate rich in arabinose with the soluble dietary fiber I sugar liquor prepared as above to obtain a soluble dietary fiber III comprising xylooligosaccharide and arabinose in specific proportion. Not only does it achieve the effective use of resources, but also the composition has a significant effect of lowering blood sugar and blood lipids.

Preferably, the volume ratio of the raffinate to the soluble dietary fiber I sugar liquor is 1:(1-7).

In the soluble dietary fiber III, the purity of the xylooligosaccharide is 70% or more. The xylooligosaccharide is the same as the above-mentioned xylooligosaccharide having a purity of 70% or more, and will not be repeated here.

In the present invention, the soluble dietary fiber III may also be concentrated to obtain a syrup or dried to obtain a powdered sugar. The method of concentration or drying is the same as above and will not be repeated here.

The present disclosure obtains the new product by compounding the raffinate, reuses the raffinate, achieves the effective use of the resource, improves the clean production level and has a good industrial utilization prospect.

In order to further illustrate the present disclosure, the soluble dietary fiber provided by the present disclosure and the preparation method thereof will be described in detail with reference to the following examples.

EXAMPLE 1

The corn cob raw material was pulverized into particles with a particle size of 2 cm, placed in a continuous countercurrent extractor, ethanol is added in such an amount that the ratio of the raw material to ethanol was 1 g:5 mL, the controlled temperature is 40° C., the extraction time was 30 minutes. And then the solid material and the leach liquor rich in pigments and monosaccharides were efficiently separated by continuous solid-liquid separations, and ethanol was recycled for reuse. The components of the leach liquor were detected, conditions of the detection were: the chromatography column was Shodex sugar KS-802, the mobile phase was ultrapure water and the column temperature was 80° C. In the high performance liquid chromatogram of the leach liquor, the percentage of peak area of various substances is shown in Table 1. Table 1 is the summary of the components the leach liquors of Examples 1-2 of the present disclosure.

The solid material was pushed into a transverse pipe through a screw conveyor, a material plug was formed, steam was directly introduced, they were thoroughly mixed under the tumbling action of the screw conveying and the steam, the steaming pressure was 0.6 MPa, the steaming time was 20 minutes, such that the hemicellulose efficiently dissolved from the raw material, a dissolution solution and steamed materials (i.e., the products in the table) were obtained. The components of them were detected, the conditions of detection were: the chromatography column was Shodex sugar KS-802, the mobile phase was ultrapure water and the column temperature was 80° C. In the high performance liquid chromatogram, the percentage of peak area of various substances is shown in Table 2. Table 2 is the summary of the components of the dissolution solutions and steamed materials of Examples 1-2 of the present disclosure.

The steamed material was subjected to pressure relief and was sprayed into an enzymolysis tank, and water was added to the enzymolysis tank such that the mass ratio of the material to process water was 1:8, and the pH was adjusted to 4.0. Xylanase was added in a unit of activity of $3 \times 10^4$ U of xylanase per kilogram of dry matter, the enzymolysis temperature was 65° C., the enzymolysis time was 14 h. After the completion of the enzymolysis reaction, the temperature was heated to 90° C., the heat was preserved for 50 minutes, the xylanase was inactivated. Then by a filtration through a rotary vacuum drum, a soluble dietary fiber crude sugar liquor and filter residue were obtained.

Into the prepared cure sugar liquor, activated carbon was added in an amount of 0.3% by weight of the crude sugar liquor, decolorization temperature was 80° C., decolorization time was 30 minutes. After the completion of the decolorization, the mixture was filtered through a plate and frame filter at a speed of 12.5 m³/h, the light transmittance was controlled to be greater than 50%. The filtrate was subjected to ion exchange, the light transmittance of the ion exchange solution was controlled to be greater than 70%, and the conductivity was less than 50 μs/cm. After removing macromolecular sugars by ultrafiltration, a soluble dietary fiber sugar liquor was obtained.

Figure 2:
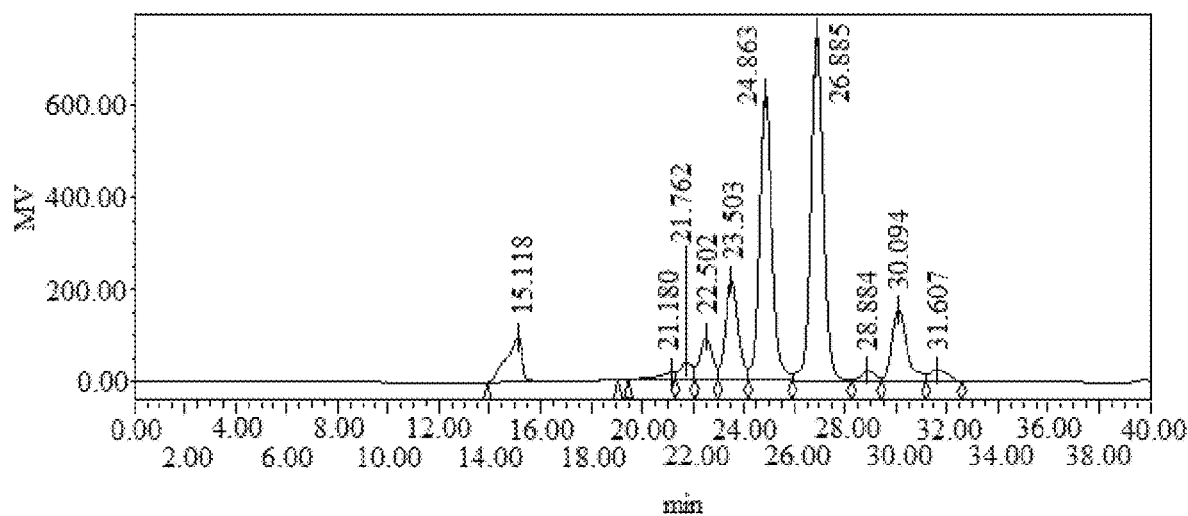
FIG. 2 is an HPLC profile of product A prepared in Example 1 of the present disclosure.

The above-mentioned soluble dietary fiber sugar liquor was divided into three portions. The first portion was concentrated with a triple effect evaporator to obtain a product syrup, the temperatures of the triple effect evaporator were as follows: the temperature of the first effect was 85° C., the temperature of the second effect was 75° C., and the temperature of the third effect was 65° C. A xylooligosaccharide syrup was prepared and designated as product A, and its purity was detected by HPLC. The results are shown in FIG. 2. FIG. 2 is the HPLC profile of product A. The component of product A is shown in Table 6, the purity of xylooligosaccharide ($X_{2-7}$) was 87.59%, and the content of xylobiose and xylotriose ($X_{2-3}$) was 69.84%. Table 6 shows the comparison of the components of the products prepared in Examples 1-2 and Comparative Examples 1-2.

Figure 3:
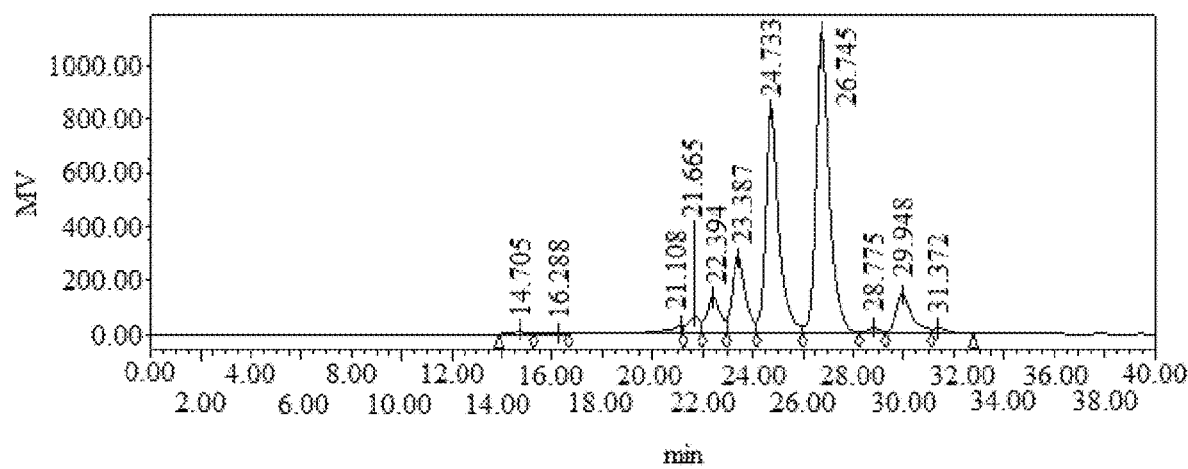
FIG. 3 is an HPLC profile of product B prepared in Example 1 of the present disclosure.

The second portion was subject to vacuum belt drying, the parameters were: the temperature of the first section was 100° C., the heating temperature of the second section was 105° C., the heating temperature of the third section was 90° C., the cooling zone temperature was 20° C., the vacuum degree was −0.085 MPa, the cloth speed was 42 L/h, the coating thickness was 0.5 cm, and the belt speed was 30 m/h. A xylooligosaccharide powdered sugar was prepared and designated as product B, and its purity was detected by HPLC. The results are shown in FIG. 3. FIG. 3 is the HPLC profile of product B. The composition of product B is shown in Table 6, the purity of xylooligosaccharide ($X_{2-7}$) was 89.56%, and the content of xylobiose and xylotriose ($X_{2-3}$) was 70.65%. Table 6 shows the comparison of the components of the products prepared in Examples 1-2 and Comparative Examples 1-2.

Figure 4:
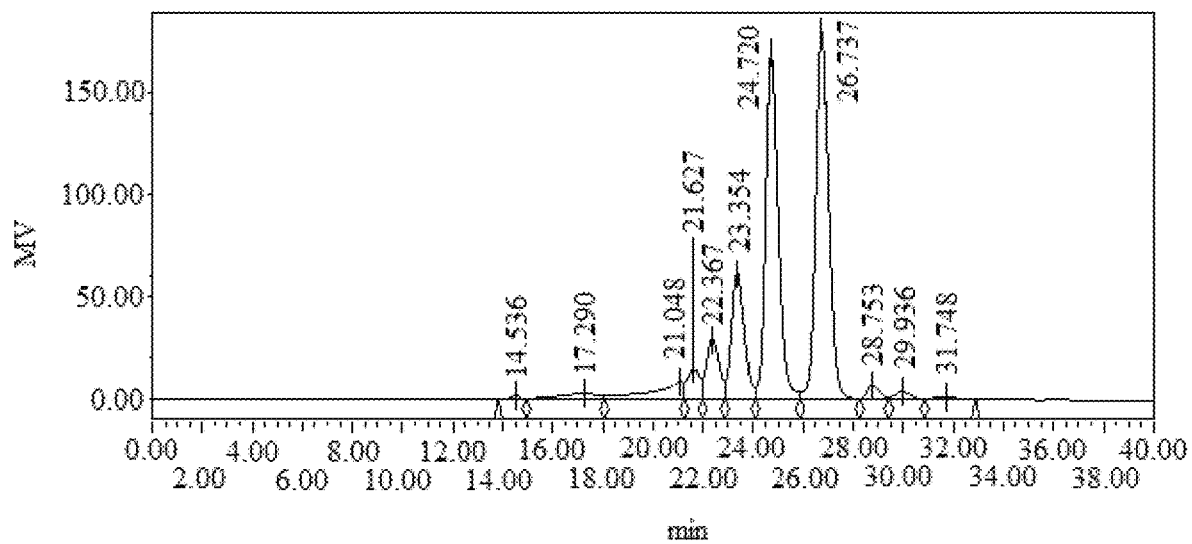
FIG. 4 is an HPLC profile of product C prepared in Example 1 of the present disclosure.
Figure 5:
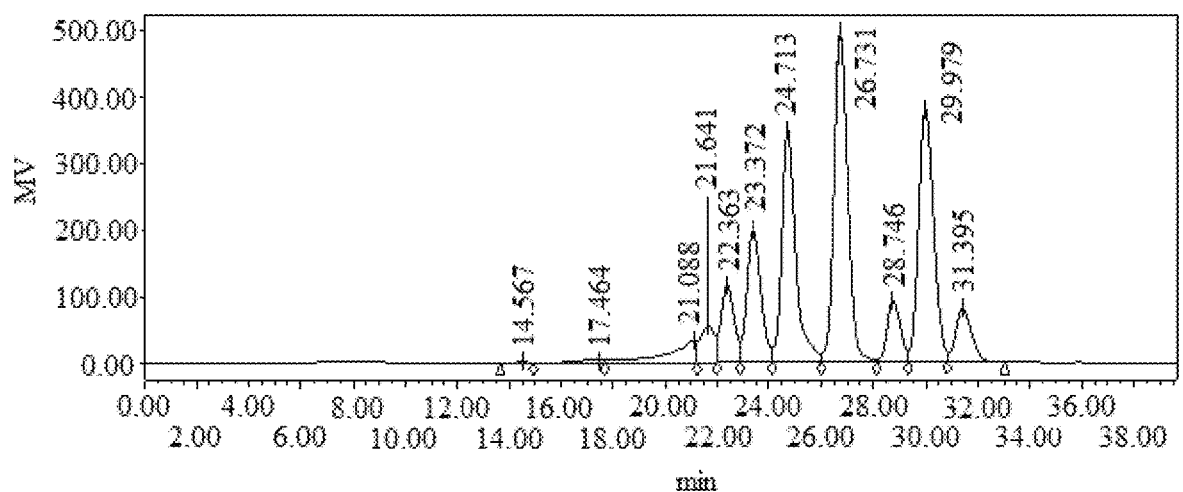
FIG. 5 is an HPLC profile of product D prepared in Example 1 of the present disclosure.

The third portion was subjected to chromatographic separation, through a simulated moving bed chromatographic separation system, the controlled feed rate was 0.3 m³/h, the system pressure was 0.9 MPa, and mass fraction of the sugar in the feed liquid was 50%, a soluble dietary fiber II and raffinate were obtained. The prepared soluble dietary fiber II was spray dried and a high component xylooligosaccharide powdered sugar was obtained and designated as product C, the spray drying hot air inlet temperature was 160° C., the outlet temperature was 100° C., and the material flow was 0.9 m³/h. Its purity was detected by HPLC. The results are shown in FIG. 4. FIG. 4 is the HPLC profile of product C. The component of product C is shown in Table 6, the purity of xylooligosaccharide ($X_{2-7}$) was 97.27%, and the content of xylobiose and xylotriose ($X_{2-3}$) was 71.39%. Table 6 shows the comparison of the compoents of the products prepared in Examples 1-2 and Comparative Examples 1-2. The soluble dietary fiber sugar liquor and the raffinated after the chromatographic separation were compounded in a volume ratio of 1:5. The compounded sugar liquor was subject to vacuum belt drying and a low component xylooligosaccharide powdered sugar was obtained and designated as product D. The operating parameters of the vacuum belt dryer were: the temperature of the first section was 100° C., the heating temperature of the second section was 105° C., the heating temperature of the third section was 90° C., the cooling zone temperature was 20° C., the vacuum degree was −0.085 MPa, the cloth speed was 42 L/h, the coating thickness was 0.5 cm, and the belt speed was 25 m/h. The purity of product D was detected by HPLC, and the results are shown in FIG. 5. FIG. 5 is the HPLC profile of product D. The component of product D is shown in Table 6, the purity of xylooligosaccharide ($X_{2-7}$) was 70.49%, and the content of xylobiose and xylotriose ($X_{2-3}$) was 48.93%. Table 6 shows the comparison of the components of the products prepared in Examples 1-2 and Comparative Examples 1-2.

The xylanase used in this example was produced by *Trichoderma reesei*, the strain number: CICC 13052, purchased from China Center of Industrial Culture Collection. The xylanase was prepared by fermentation with the strain and purification. The specific preparation method was: 2 wt % to 6 wt % of corncob (20 to 80 mesh); 0.25 wt % to 0.5 wt % of xylooligosaccharide; 0.25 wt % to 1 wt % of yeast extract; 0.25 wt % to 1 wt % of peptone; 0.25 wt % to 0.5 wt % of yeast powder; 0.02 wt % to 0.06 wt % of $KH_2PO_4$; 0.02 wt % to 0.05 wt % of $MgSO_4.7H_2O$; 0.01 wt % of $FeSO_4$, initial pH 6.0, an enzyme-producing medium was prepared. The strain was inoculated in the enzyme-producing medium, 28° C. to 32° C., fermented for 64 h to 84 h, the culture was filtrated through a plate and frame filter, the solid was separated from the liquid, an xylanase crude enzyme solution was obtained. The crude enzyme solution was concentrated 10-fold to 50-fold by ultrafiltration, and separated with gel filtration chromatography (Sephdex G-75), 20,000-90,000 Da protein was collected, i.e., endo-xylanase.

TABLE 1

Summary of the Components of the Leach Liquors of Examples 1-2 of the Present Disclosure

| items | Pigments/wt % | Xylotriose/wt % | Xylobiose/wt % | Glucose/wt % | Xylose/wt % | Arabinose/wt % |
|---|---|---|---|---|---|---|
| Example 1 | 64.72 | 1.53 | 1.87 | 12.14 | 16.35 | 2.47 |
| Example 2 | 63.85 | 1.64 | 1.92 | 7.45 | 14.31 | 2.23 |

TABLE 2

Components of the Dissolution Solutions and the Products of Examples 1-2 of the Present Disclosure and Comparative Example 1.

| Items | Comparative example 1 | | Example 1 | | Example 2 | |
|---|---|---|---|---|---|---|
| | Dissolution solution | Product | Dissolution solution | Product | Dissolution solution | Product |
| high polysaccharides | 49.8 | — | 61.51 | — | 53.09 | — |
| Xyloheptaose | 3.18 | 5.21 | 4.21 | 1.07 | 5.38 | 0.95 |
| Xylohexaose | 3.38 | 4.35 | 3.98 | 1.94 | 5.7 | 0.78 |
| Xylopentaose | 3.98 | 4.94 | 3.97 | 4.65 | 5.44 | 1.98 |
| Xylotetraose | 5.3 | 10.98 | 4.15 | 10.09 | 5.74 | 5.9 |
| Xylotriose | 7.4 | 19.45 | 4.02 | 30.91 | 5.13 | 27.5 |
| Xylobiose | 8.19 | 25.33 | 5.57 | 38.93 | 6.09 | 44.52 |
| Cellobiose | — | 1.85 | — | — | — | — |
| Glucose | 3.43 | 5.33 | 1.13 | 2.52 | 0.89 | 3.65 |
| Xylose | 7.53 | 13.85 | 5.41 | 6.01 | 6.18 | 8.81 |
| Arabinose | 6.79 | 8.71 | 5.84 | 3.88 | 5.94 | 5.91 |
| The proportion of xylobiose-xylotetraose | | 55.76 | | 79.93 | | 77.92 |
| Dissolved solids | 3.50% | | 4.00% | | 4.00% | |

In which: "—" means it was not detected; high polysaccharides means the glycan with a degree of polymerization >7.

As can be seen from Table 1 and Table 2, the present disclosure removes most of the monosaccharides by using continuous countercurrent leaching technology, at the same time adopts continuous steaming technique processing in a transverse pipe, such that in the dissolution solution the content of high polysaccharides increases, the content of monosaccharides such as glucose, xylose and arabinose decreases, which in turn affects the components of the product after enzymolysis process, meanwhile the dissolution rate of hemicellulose xylan is increased and the amount of xylanase used is reduced.

EXAMPLE 2

The corncob raw material was pulverized into particles with a particle size of 4 cm, placed in a continuous countercurrent extractor, KOH aqueous solution with a mass concentration of 0.5% was added in such an amount that the ratio of the raw material to aqueous solution was 1 g:8 mL, the controlled temperature was 70° C., the extraction time was 40 minutes. And then the solid material and the leach liquor rich in pigments and monosaccharides were efficiently separated by continuous solid-liquid separations.

The solid material was pushed into a transverse pipe through a screw conveyor, a material plug was formed, steam was directly introduced, they were thoroughly mixed under the tumbling action of the screw conveying and the steam, the steaming pressure was 0.4 MPa, the steaming time was 50 minutes, such that the hemicellulose efficiently dissolved from the raw material. The steamed material was subjected to pressure relief and was sprayed into an enzymolysis tank, and process water was added to the enzymolysis tank such that the mass ratio of steamed material to the process water was 1:6, the pH value was adjusted to 5.5. Xylanase was added in a unit of activity of $4 \times 10^4$ U of xylanase per kilogram of dry sold material, enzymolysis temperature was 50° C., enzymolysis reaction time was 8 h. After the completion of the enzymolysis reaction, the temperature was heated to 95° C., the heat was preserved for 30 minutes, the xylanase was inactivated. Then by a filtration through a belt dryer, a soluble dietary fiber crude sugar liquor and filter residue were obtained.

Into the prepared cure sugar liquor, activated carbon was added in an amount of 0.36% by weight of the crude sugar liquor, decolorization temperature was 80° C., decolorization time was 30 minutes. After the completion of the decolorization, the mixture was subjected to solid-liquid separation at a speed of 13.75 m³/h, the light transmittance of the filtrate was controlled to be greater than 50%. The filtrate was subjected to ion exchange, the light transmittance of the ion exchange solution was controlled to be greater than 70%, and the conductivity was less than 50

μs/cm. After removing macromolecular sugars by ultrafiltration, a soluble dietary fiber sugar liquor was obtained.

Figure 6:
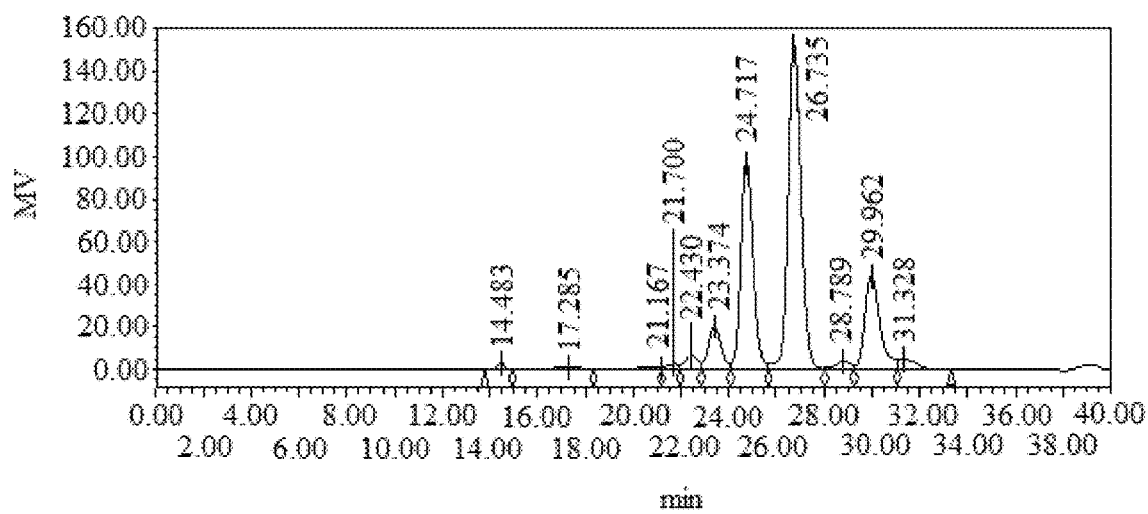
FIG. 6 is an HPLC profile of product E prepared in Example 2 of the present disclosure.
Figure 7:
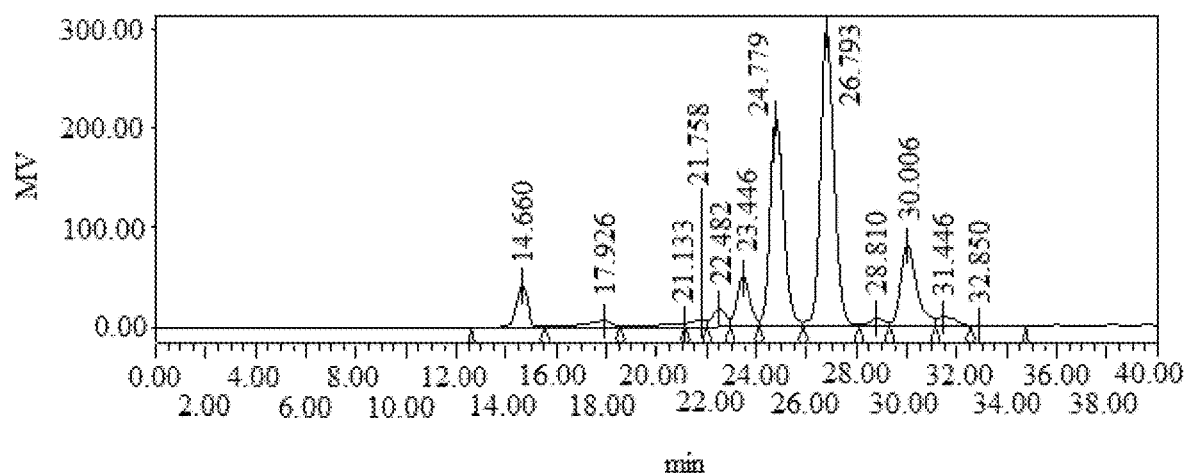
FIG. 7 is an HPLC profile of product F prepared in Example 2 of the present disclosure.
Figure 8:
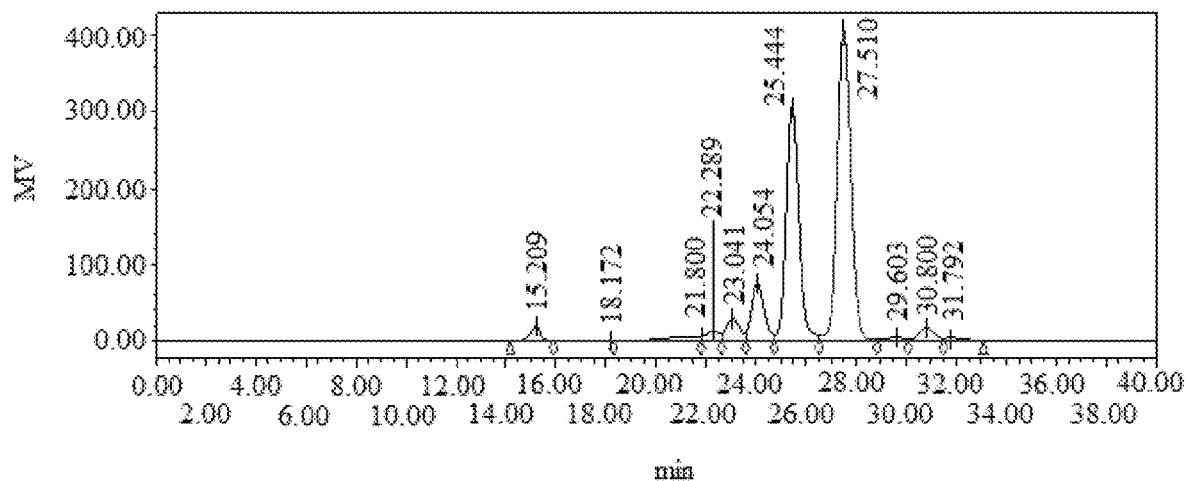
FIG. 8 is an HPLC profile of product G prepared in Example 2 of the present disclosure.
Figure 9:
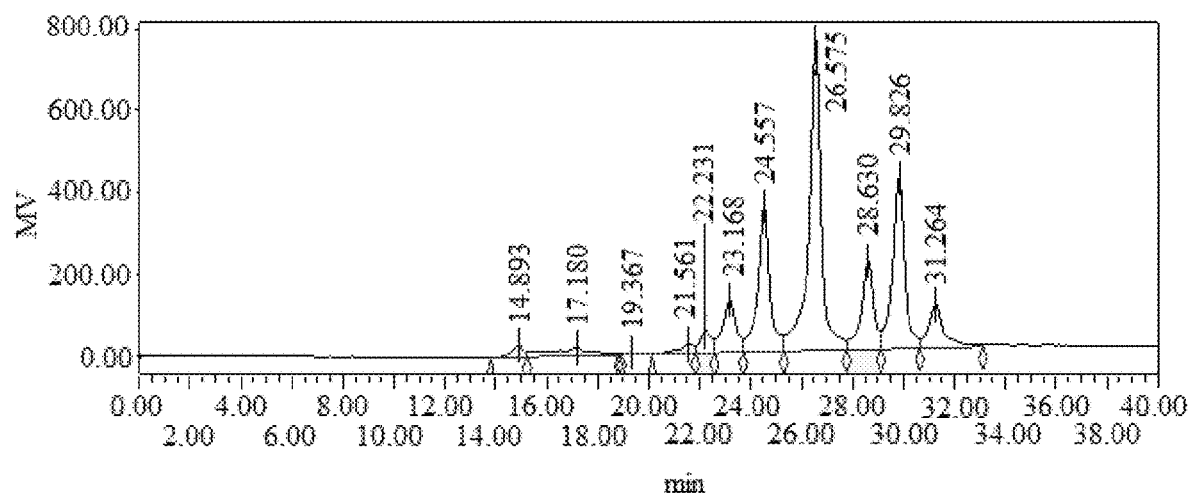
FIG. 9 is an HPLC profile of product H prepared in Example 2 of the present disclosure.

The soluble dietary fiber sugar liquor was divided into three portions. The first portion was concentrated with a triple effect evaporator, a product syrup was obtained, and designated as product E, the temperatures of the triple effect evaporator were: the temperature of the first effect was 90° C., the temperature of the second effect was 80° C., and the temperature of the third effect was 70° C. Its purity was detected by HPLC. The results are shown in FIG. 6. FIG. 6 is the HPLC profile of product E. The componnet of product E is shown in Table 6, the purity of xylooligosaccharide ($X_{2-7}$) was 81.63%, and the content of xylobiose and xylotriose ($X_{2-3}$) was 72.02%. Table 6 shows the comparison of the components of the products prepared in Examples 1-2 and Comparative Examples 1-2. The second portion was subjected to vacuum rake drying to obtain a xylooligosaccharide powdered sugar, and designated as product F. The operating parameters were: the heating temperature was 95° C., the vacuum degree was −0.090 MPa, and the rake tooth speed was 6 rpm. Its purity was detected by HPLC. The results are shown in FIG. 7. FIG. 7 is the HPLC profile of product F. The component of product F is shown in Table 6, the purity of xylooligosaccharide ($X_{2-7}$) was 82.53%, and the content of xylobiose and xylotriose ($X_{2-3}$) was 70.76%. Table 6 shows the comparison of the components of the products prepared in Examples 1-2 and Comparative Examples 1-2. The third portion was subjected to chromatographic separation through a simulated moving bed chromatographic separation system, in which the controlled feed rate was 0.25 m$^3$/h, the system pressure was 1.0 MPa, and the mass fraction of the sugar in the feed liquid was 56%. The high component raffinate after the chromatography was subject to vacuum belt drying preparing a high component xylooligosaccharide powdered sugar, and was designated as product G The operating parameters of the vacuum belt dryer were: the temperature of the first section was 105° C., the heating temperature of the second section was 110° C., the heating temperature of the third section was 95° C., the cooling zone temperature was 25° C., the vacuum degree was −0.090 MPa, the cloth speed was 42 L/h, the coating thickness was 0.3 cm, and the belt speed was 25 m/h. Its purity was detected by HPLC. The results are shown in FIG. 8. FIG. 8 is the HPLC profile of product G The component of product G is shown in Table 6, the purity of xylooligosaccharide ($X_{2-7}$) was 97.15%, and the content of xylobiose and xylotriose ($X_{2-3}$) was 73.29%. Table 6 shows the comparison of the components of the products prepared in Examples 1-2 and Comparative Examples 1-2. After the chromatographic separation, the raffinate and the soluble dietary fiber sugar liquor were compounded in a volume ratio of 1:7. The compounded sugar liquor was subject to vacuum rake drying and a low component xylooligosaccharide powdered sugar was obtained, and was designated as product H. The operating parameters of the vacuum rake dryer were: the heating temperature was 90° C., the vacuum degree was −0.090 MPa, and the rake tooth speed was 8 rpm. Its purity was detected by HPLC. The results are shown in FIG. 9. FIG. 9 is the HPLC profile of product H. The component of product H is shown in Table 6, the purity of xylooligosaccharide ($X_{2-7}$) was 70.49%, and the content of xylobiose and xylotriose ($X_{2-3}$) was 48.74%. Table 6 shows the comparison of the components of the products prepared in Examples 1-2 and Comparative Examples 1-2.

The xylanase used in this example was the same as that in Example 1.

COMPARATIVE EXAMPLE 1

The corncob raw material was pulverized into particles with a particle size of 0.5 cm, and subjected to high-temperature steaming, the solution was process water, the temperature was 150° C., the time was 40 minutes.

The steamed material was subjected to pressure relief and was sprayed into an enzymolysis tank, and process water was added to the enzymolysis tank such that the mass ratio of steamed material to process water was 1:6, and the pH value was adjusted to 5.5. Xylanase was added in a unit of activity of 1×10$^5$ U of xylanase per kilogram of dry sold material, food grade 200,000 U/g xylanase commercially available from Henan Yangshao Bio-Products Co., Ltd., the enzymolysis temperature was 50° C., the enzymolysis time was 8 h. After the completion of the enzymolysis reaction, the temperature was heated to 95° C., the heat was preserved for 30 minutes, the xylanase was inactivated. Then by filtration through a belt dryer, a soluble dietary fiber crude sugar liquor and filter residue were obtained.

Figure 10:
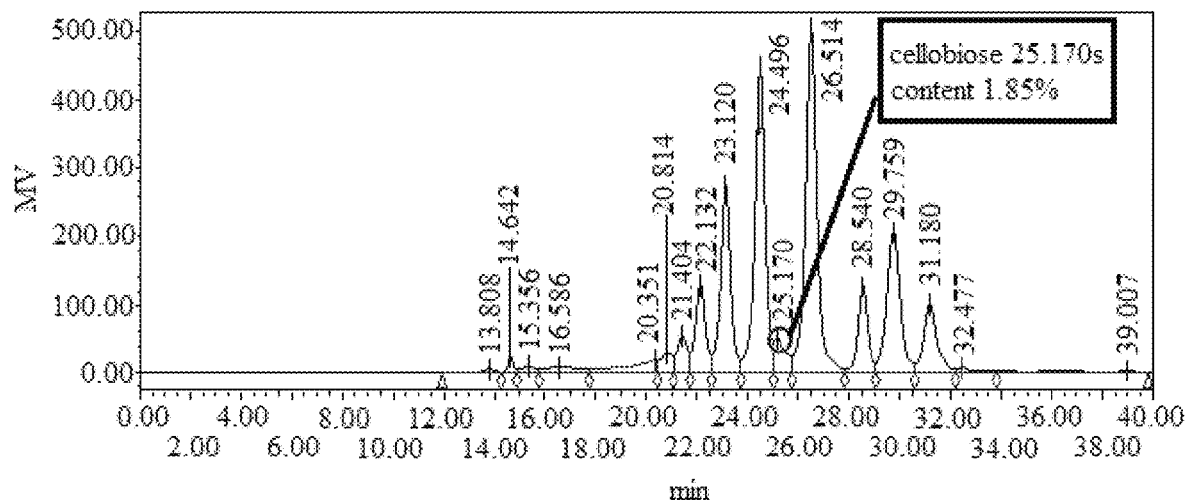
FIG. 10 is an HPLC profile of the product prepared in Comparative Example 1, it can be found that the content of the cellobiose is 1.85% according to the absorption peak of cellobiose at 25.170 s.

Into the prepared crude sugar liquor, activated carbon was added in an amount of 0.6% by weight of the crude sugar liquor, the decolorization temperature was 80° C., the decolorization time was 30 minutes. After the completion of the decolorization, the mixture was subjected to solid-liquid separation at a speed of 6.25 m$^3$/h, the light transmittance of the filtrate was controlled to be greater than 50%. The filtrate was subjected to ion exchange, the light transmittance of the ion exchange solution was controlled to be greater than 70%, and the conductivity was less than 50 μs/cm. After removing macromolecular sugars by ultrafiltration, a soluble dietary fiber sugar liquor was obtained. A xylooligosaccharide syrup was prepared and its purity was detected by HPLC. FIG. 10 is the HPLC profile of the above-mentioned product. According to the absorption peak of cellobiose at 25.170 s, it can be found that the content of cellobiose was 1.85%. The component of the product is shown in Table 6, the purity of xylooligosaccharide ($X_{2-7}$) was 70.26%, and the content of xylobiose and xylotriose ($X_{2-3}$) was 44.78%. Table 6 shows the comparison of the components of the products prepared in Examples 1-2 and Comparative Examples 1-2.

COMPARATIVE EXAMPLE 2

The corncob raw material was pulverized into particles with a particle size of 1 cm, and subjected to steam explosion pretreatment, the parameters were: the pressure was 1.5 MPa, the pressure was preserved for 3 minutes. The pretreated material was subjected to pressure relief and was sprayed into an enzymolysis tank, and process water was added to the enzymolysis tank such that the mass ratio of steamed material to process water was 1:6, and the pH value was adjusted to 5.5. Xylanase was added in a unit of activity of 9×10$^4$ U of xylanase per kilogram of dry sold material, food grade 200,000 U/g xylanase commercially available from Henan Yangshao Bio-Products Co., Ltd., the enzymolysis temperature was 50° C., the enzymolysis time was 8 h. After the completion of the enzymolysis reaction, the temperature was heated to 95° C., the temperature was preserved for 30 minutes, the xylanase was inactivated. Then by filtration through a belt dryer, a soluble dietary fiber crude sugar liquor and filter residue were obtained.

Figure 11:
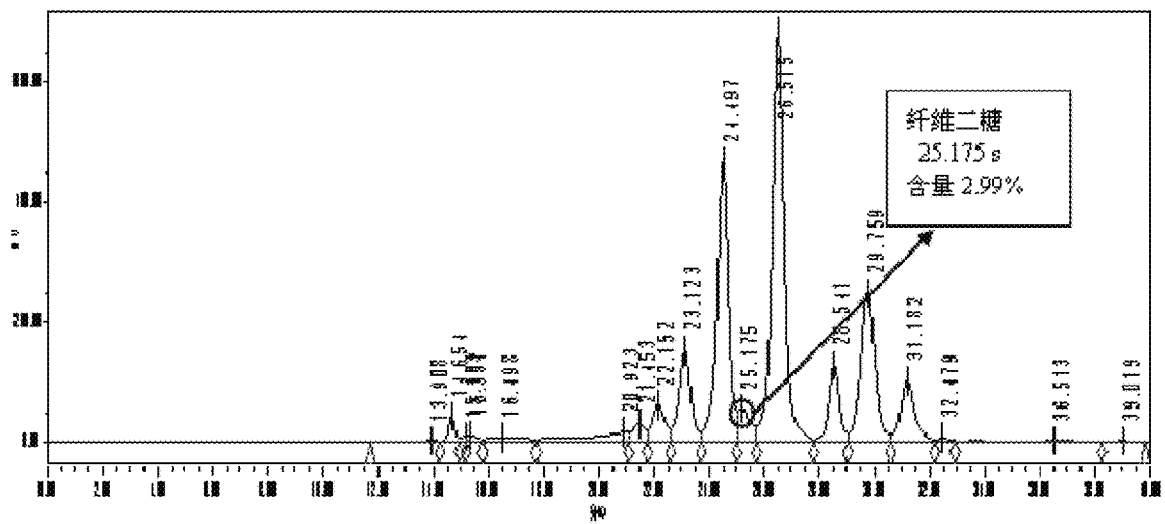
FIG. 11 is an HPLC profile of the product prepared in Comparative Example 2, it can be found that the content of the cellobiose is 2.99% according to the absorption peak of cellobiose at 25.175 s.
Figure 12:
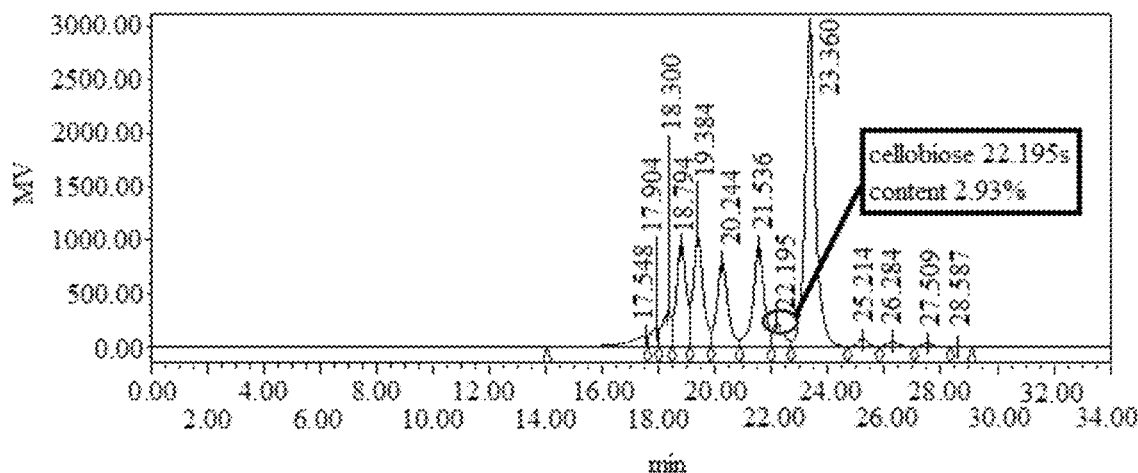
FIG. 12 is an HPLC profile of a foreign product, it can be found that the content of the cellobiose is 2.93%, according to the absorption peak of cellobiose at 22.195 s.

Into the prepared cure sugar liquor, activated carbon was added in an amount of 0.8% by weight of the crude sugar liquor, the decolorization temperature was 80° C., the decolorization time was 30 minutes. After the completion of the decolorization, the mixture was subjected to solid-liquid separation at a speed of 7.5 m³/h, the light transmittance of the filtrate was controlled to be greater than 50%. The filtrate was subjected to ion exchange, the light transmittance of the ion exchange solution was controlled to be greater than 70%, and the conductivity was less than 50 μs/cm. After removing macromolecular sugars by ultrafiltration, a soluble dietary fiber sugar liquor was obtained. A syrup was prepared and its purity was detected by HPLC. FIG. 11 is the HPLC profile of the product. According to the absorption peak of cellobiose at 25.175 s, it can be found that the content of cellobiose was 2.99%. The component of the product is shown in Table 6, the purity of xylooligosaccharide ($X_{2-7}$) was 70.23%, and the content of xylobiose and xylotriose ($X_{2-3}$) was 42.79%. Table 6 shows the comparison of the components of the products prepared in Examples 1-2 and Comparative Examples 1-2.

EXAMPLE 3

1) The added amounts of the activated carbon and the filtration rate of Examples 1-2 and Comparative Examples 1-2 were compared, and the results are shown in Table 3. Table 3 is the comparison of the added amounts of the activated carbon and the filtration rate of Examples 1-2 and Comparative Examples 1-2.

TABLE 3

Comparison of the Added Amounts of the Activated Carbon and the Filtration Rate of Examples 1-2 and Comparative Examples 1-2

|  | Added amounts of the activated carbon (%) | Filtration rate of the material solution through a plate and frame filter (m³/h) |
| --- | --- | --- |
| Example 1 | 0.3% | 12.5 |
| Example 2 | 0.36% | 13.75 |
| Comparative Example 1 | 0.6% | 6.25 |
| Comparative Example2 | 0.8% | 7.5 |

From Table 3, it can be found that after continuous countercurrent leaching treatment, the amount of activated carbon added in decolorization process reduces by 40%-50%, the filtration rate of the material solution through a plate and frame filter increases by 100%-120%. The decolorization cost is reduced and the production efficiency is improved.

2). The added amounts of the xylanase of Examples 1-2 and Comparative Examples 1-2 were compared, and the results are shown in Table 4. Table 4 is the comparison of the added amounts of the xylanase of Examples 1-2 and Comparative Examples 1-2.

TABLE 4

Comparison of the Added Amounts of the Xylanase of Examples 1-2 and Comparative Examples 1-2

| Items | Added amounts of the xylanase (U/kg dry matter raw material) |
| --- | --- |
| Example 1 | $3 \times 10^4$ U |
| Example 2 | $4 \times 10^4$ U |
| Comparative Example 1 | $1 \times 10^5$ U |
| Comparative Example 2 | $9 \times 10^4$ U |

From Table 4, it can be found that the invention makes the hemicellulose long chain structure of the corncob break into hemicellulose short chain by continuous steaming processing in a transverse pipe pretreatment, it is more conducive to enzymolysis of xylanase, reduces the added amount of the xylanase and the production cost.

3). Product A, Product E of the Examples and the soluble dietary fiber sugar liquor prepared in Comparative Examples 1 and 2 were diluted to a solution with a certain mass concentration of sugar (solid content), and the absorbance at 280 nm and 420 nm was measured with a 1 cm cuvette. The specific results are shown in Table 5. Table 5 shows the comparison of the color values of the sugar liquor prepared in Examples 1-2 and Comparative Examples 1-2.

TABLE 5

Comparison of the Color Values of the Sugar Liquor Prepared of Examples 1-2 and Comparative Examples 1-2

| Items | Solid content | Absorbance value at 280 nm | Absorbance value at 420 nm |
| --- | --- | --- | --- |
| Example 1 | 50% | 0.833 | 0.0518 |
|  | 37.5% | 0.703 | 0.0469 |
| Example 2 | 50% | 0.845 | 0.0523 |
|  | 37.5% | 0.691 | 0.0471 |
| Comparative Example1 | 50% | 2.112 | 0.125 |
|  | 37.5% | 2.005 | 0.129 |
| Comparative Example 2 | 50% | 1.10 | 0.07 |
|  | 37.5% | 0.85 | 0.06 |

From Table 5, it can be found that the absorbance values at 280 nm and 420 nm of the xylooligosaccharide syrup prepared in the present disclosure were significantly decreased, which indicates that the color and luster of the xylooligosaccharide product prepared by the present disclosure is reduced.

In the present disclosure, the absorbance value of the sugar liquor with a concentration of 37.5% at 280 nm reduced by 17.29% to 18.07%, and the absorbance value at 420 nm reduced by 25.25% to 26.0%. In the present disclosure, the absorbance value of the sugar liquor with a concentration of 50% at 280 nm reduced by 23.18% to 24.27%, and the absorbance value at 420 nm reduced by 21.50% to 21.83%. The color value of the xylooligosaccharide solution decreases, the taste of the product is softer and sweeter, successfully solves the application problem of using xylooligosaccharide in certain field caused by the deep color and luster, and broadens the application of xylooligosaccharides 4) The component of the products prepared in Examples 1-2 and Comparative Examples 1 to 2 were compared, and the result is shown in Table 6. Table 6 is the comparison of the component of the products prepared in Examples 1 to 2 and Comparative Examples 1 to 2.

TABLE 6

Component of the Products Prepared of Examples 1 to 2 and Comparative Examples 1 to 2

| Items | $X_{2-7}$ % | $X_7$ % | $X_6$ % | $X_5$ % | $X_4$ % | $X_{2-3}$ % | $X_3$ % | $X_2$ % | $G_2$ % |
|---|---|---|---|---|---|---|---|---|---|
| Product A | 87.59 | 1.07 | 1.94 | 4.65 | 10.09 | 69.84 | 30.91 | 38.93 | |
| Product B | 89.56 | 1.1 | 2.21 | 5.09 | 10.51 | 70.65 | 30.44 | 40.21 | |
| Product C | 97.27 | 1.27 | 3.01 | 5.96 | 15.64 | 71.39 | 33.84 | 37.55 | |
| Product D | 70.49 | 1.42 | 3.23 | 5.65 | 11.26 | 48.93 | 22.55 | 26.38 | |
| Product E | 81.63 | 0.95 | 0.78 | 1.98 | 5.9 | 72.02 | 27.5 | 44.52 | |
| Product F | 82.53 | 1.1 | 1.1 | 2.6 | 6.97 | 70.76 | 28.68 | 42.08 | |
| Product G | 97.15 | 1.37 | 2.11 | 5.84 | 14.54 | 73.29 | 34.74 | 38.55 | |
| Product H | 70.49 | 1.72 | 3.03 | 5.85 | 11.15 | 48.74 | 18.66 | 30.08 | |
| Comparative Example 1 | 70.26 | 5.21 | 4.35 | 4.94 | 10.98 | 44.78 | 19.45 | 25.33 | 1.85 |
| Comparative Example 2 | 70.23 | 4.07 | 4.86 | 6.7 | 11.81 | 42.79 | 18.6 | 24.19 | 2.99 |
| Foreign product | 90.35 | 3.53 | 11.54 | 12.78 | 10.85 | 51.65 | 12.93 | 38.72 | 2.93 |

In which:
$X_{2-7}$ is the purity (content) of xylooligosaccharides;
$X_{2-3}$ is the total content of xylobiose and xylotriose;
$X_7$ is the total content of xyloheptaose and xylooligosaccharide with more degree of polymerization;
$X_6$ is the content of xylohexaose;
$X_5$ is the content of xylopentaose;
$X_4$ is the content of xylotetraose;
$X_3$ is the content of xylotriose;
$X_2$ is the content of xylobiose; and
$G_2$ is the content of cellobiose.

The foreign product was a xylooligosaccharide commercially available from Japan.

Products A-H were products of Examples 1 and 2. Comparative Example 1 used the syrup obtained by concentrating the soluble dietary fiber sugar liquor prepared in Comparative Example 1. Comparative Example 2 used the powdered sugar obtained by spray-drying the soluble dietary fiber sugar liquor prepared in Comparative Example 2.

From Table 6, it can be found that in the soluble dietary fiber product prepared by the present disclosure, none of them contains cellobiose according to the detection; while the xylooligosaccharide syrup prepared in Comparative Example 1, the xylooligosaccharide powdered sugar prepared in Comparative Example 2, and the xylooligosaccharide product commercially available from Japan all contain about 2% of cellobiose. By screening appropriate xylanase, the proportion of xylobiose and xylotriose in the prepared dietary fiber I and II of the present invention are all more than ≥70%, while the proportion of xylobiose and xylotriose in the foreign product with 90% purity is 51.65%; and the proportion of xylobiose and xylotriose in the dietary fiber III are all ≥48%, while was between 42.79% and 44.78% in the products prepared in Comparative Examples. In the xylooligosaccharide products prepared in the present disclosure, the proportion of xyloheptaose in the xylooligosaccharide are all about 1%, while in the xylooligosaccharide products prepared in comparative examples, the proportion of xyloheptaose are between 5% to 10%, in the products commercially available from Japan, the proportion of xyloheptaose and xylooligosaccharide with more degree of polymerization is 3.35%.

Therefore, by screening appropriate xylanase, the present disclosure optimizes the composition of the functional components of the product, improves the proportion of the functional components, which are mainly xylobiose and xylotriose, and reduces the production of cellobiose and miscellaneous sugars such as polysaccharides with a degree of polymerization greater than or equal to seven, obtains a new product with a higher quality than the commercially available products.

The products prepared in Examples 1-2 and Comparative Examples 1-2 were prepared into solutions with low concentration of xylose of 1-10 mg/ml, HCL or $H_2SO_4$ was used as an acidifying agent, hydrogen ion concentration was about 0.6 mol/L, it was hydrolyzed at 100° C. for 90 minutes. Then the temperature was reduced and the pH was adjusted to a range suitable for chromatography column. The condition of the content of glucose, xylose, and arabinose produced by the acidolysis of each product were statistically compared. The results are shown in Table 7. Table 7 is the comparison of the monosaccharides after the acidolysis of the products prepared in Examples 1-2 and Comparative Examples 1-2.

TABLE 7

Comparison of the Monosaccharides after the Acidolysis of the Products Prepared of Examples 1-2 and Comparative Examples 1-2

| Item | Glucose (wt %) | Xylose (wt %) | Arabinose (wt %) |
|---|---|---|---|
| Product A | 4.28 | 86.97 | 8.26 |
| Product B | 4.73 | 85.9 | 7.62 |
| Product C | 8.87 | 87.92 | 2.91 |
| Product D | 6.16 | 84.09 | 8.75 |
| Product E | 5.13 | 84.97 | 7.59 |
| Product F | 5.82 | 83.22 | 7.64 |
| Product G | 9.08 | 87.08 | 3.59 |
| Product H | 7.17 | 82.97 | 8.02 |
| Comparative Example 1 | 9.73 | 78.53 | 10.52 |
| Comparative Example 2 | 9.26 | 79.13 | 9.92 |
| Foreign product | 11.87 | 84.21 | 3.02 |

EXAMPLE 4

Figure 13:
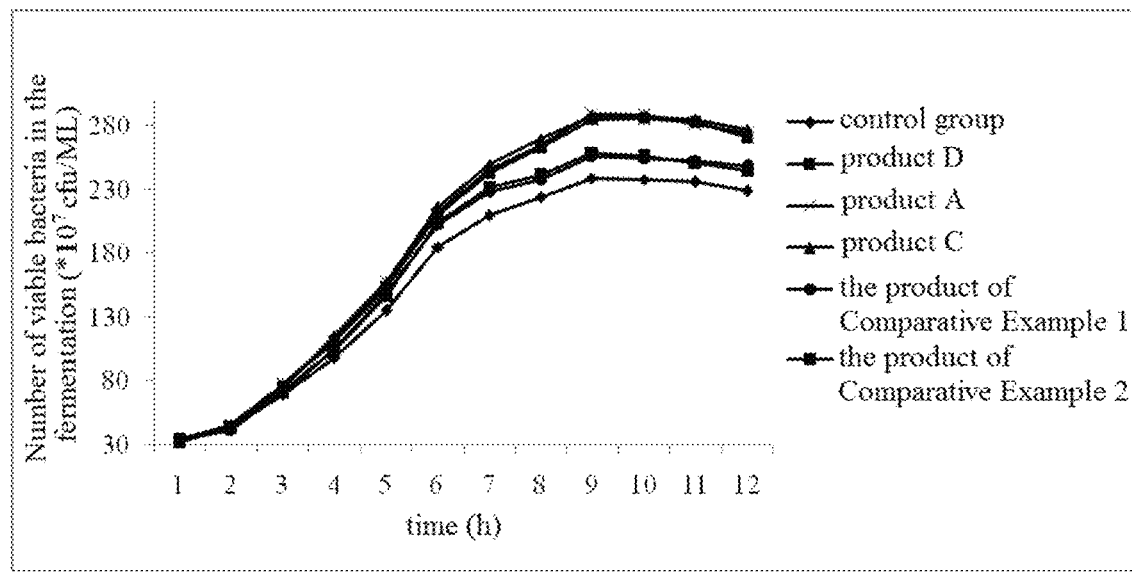
FIG. 13 shows the effect of each product in Example 4 on the proliferation of *Bifidobacterium*.

Taking products A, C, and D prepared in Example 1 and the products prepared in Comparative Examples 1 and 2, same effective content of xylooligosaccharides (the total contents of xylobiose to xyloheptaose were the same) were added according to the purity of xylooligosaccharide of each product (that is, the content of the xylooligosaccharide) of each product, then they were added into the medium of *Bifidobacterium* (basal medium), the effective content of xylooligosaccharides by weight was 0.5 wt % of the medium. In vitro culture was carried out. No xylooligosaccharide was added to the control group. The effect of the control group and each group on the proliferation of *Bifidobacterium* is shown in FIG. 13. FIG. 13 is the effect of the control group and each group on the proliferation of *Bifidobacterium*.

As can be seen from FIG. 13, the effects of the products prepared by the present disclosure on the proliferation of viable bacteria of *Bifidobacterium* are significantly higher than those of the products prepared by the Comparative Examples and the xylooligosaccharide-free control group.

EXAMPLE 5

Taking products A, C, and D prepared in Example 1 and the products prepared in Comparative Examples 1 and 2, same effective content of xylooligosaccharides (the total content of xylobiose to xyloheptaose were the same) were added according to the purity of xylooligosaccharide of each product (that is, the content of the xylooligosaccharide) of each product, that is, the total content of xylobiose to xyloheptaose were the same in each product, then they were used as sweeteners and added into soy milk products, wherein the effective added amount of xylooligosaccharides was 1 wt %. A research of the effect of each product on in vivo proliferation of *Bifidobacterium* and *Lactobacillus* and the effect of improving intestinal flora were carried out.

The randomly selected 100 people were divided into 5 groups, and each group was given 250 ml/day of soy milk supplemented with different xylooligosaccharide products. After taking for 30 days, the intestinal floras of the tested people were detected. The results are shown in Table 8. Table 8 is the detection results of the effect of each product in Example 5 on the intestinal flora in human.

From Table 8, it can be found that the xylooligosaccharides prepared by the present disclosure have better effects on the proliferation of *Bifidobacterium* and *Lactobacillus*.

EXAMPLE 6

Taking products A, C, and D prepared in Example 1 and the products prepared in Comparative Examples 1 and 2, same effective content of xylooligosaccharides (the total content of xylobiose to xyloheptaose were the same) were added according to the purity of xylooligosaccharide of each product (that is, the content of the xylooligosaccharide) of each product, that is, the total content of xylobiose to xyloheptaose were the same in each product, then they were used as sweeteners and added into mouse feed, wherein the effective added amount of xylooligosaccharides was 1 wt %. A research of the effect of each product on blood glucose in mice was carried out.

Animals and groups: 120 ICR mice were injected with alloxan 45 mg/kg.Bw in the tail vein, hyperglycemia mouse model was produced, and divided into six groups (20 mice each group). Group 1: control group, that is, common feed group; group 2: product D xylooligosaccharide was added in the feed; group 3: product A xylooligosaccharide was added in the feed; group 4: product C xylooligosaccharide was added in the feed; group 5: the xylooligosaccharide product prepared in Comparative Example 1 was added in the feed; group 6: the xylooligosaccharide product prepared in Comparative Example 2 was added in the feed, wherein the effective added amount of xylooligosaccharides was 1 wt %. After the above-mentioned mice were fed for 30 days, the fasting blood glucose (8 hours fasting) was detected, and the results are shown in table 9. After feeding experiments, the fasting blood glucose and 2 hours postprandial blood glucose (each mouse was intragastrically administered with glucose 1.5 g/kg.Bw) are shown in Table 10.

TABLE 8

Detection Results of the Effect of Each Product on the Intestinal Flora in Human
(logCFU/g X ± SD)

| | Product D | | | Product A | | | Product C | | |
|---|---|---|---|---|---|---|---|---|---|
| Bacterial | Before taking | After taking | Appreciation rate (%) | Before taking | After taking | Appreciation rate (%) | Before taking | After taking | Appreciation rate (%) |
| Enterobacteriaceae | 8.01 ± 0.41 | 8.12 ± 0.36 | 1.4 | 8.26 ± 0.57 | 8.57 ± 0.52 | 3.76 | 7.98 ± 0.42 | 8.11 ± 0.61 | 1.63 |
| *Enterococcus* | 6.53 ± 0.59 | 6.39 ± 0.24 | −2.14 | 6.64 ± 0.55 | 6.51 ± 0.63 | −1.96 | 6.59 ± 0.62 | 6.61 ± 0.48 | 0.30 |
| *Clostridium perfringens* | 1.69 ± 0.37 | 1.61 ± 0.27 | −4.73 | 1.63 ± 0.32 | 1.69 ± 0.43 | 3.68 | 1.58 ± 0.41 | 1.68 ± 0.76 | 6.33 |
| *Lactobacillus* | 7.24 ± 0.43 | 8.37 ± 0.48 | 15.61 | 7.18 ± 0.62 | 8.99 ± 0.81 | 25.21 | 7.32 ± 0.57 | 8.92 ± 0.32 | 21.86 |
| *Bifidobacterium* | 6.89 ± 0.63 | 8.83 ± 0.59 | 28.16 | 6.53 ± 0.58 | 9.07 ± 0.64 | 38.90 | 6.86 ± 0.42 | 9.11 ± 0.39 | 32.80 |

| | Comparative example 1 | | | Comparative example 2 | | |
|---|---|---|---|---|---|---|
| Bacterial | Before taking | After taking | Appreciation rate (%) | Before taking | After taking | Appreciation rate (%) |
| Enterobacteriaceae | 8.06 ± 0.38 | 8.18 ± 0.56 | 1.49 | 7.84 ± 0.40 | 8.09 ± 0.56 | 3.19 |
| *Enterococcus* | 6.47 ± 0.55 | 6.39 ± 0.61 | −1.24 | 6.61 ± 0.57 | 6.46 ± 0.49 | −2.27 |
| *Clostridium perfringens* | 1.78 ± 0.38 | 1.67 ± 0.52 | −6.18 | 1.66 ± 0.38 | 1.61 ± 0.31 | −3.01 |
| *Llactobacillus* | 7.62 ± 0.49 | 8.27 ± 0.62 | 8.53 | 7.47 ± 0.61 | 8.15 ± 0.51 | 9.10 |
| *Bifidobacterium* | 6.67 ± 0.54 | 8.53 ± 0.43 | 27.89 | 6.74 ± 0.33 | 8.37 ± 0.55 | 24.18 |

TABLE 9

Summary of the Effects of Xylooligosaccharides on Fasting Blood Glucose in Hyperglycemic Mice of Example 6 of the Present Disclosure

| Groups | Number of animals | Fasting blood glucose value (mmol/L) Before the test | Fasting blood glucose value (mmol/L) After the test | Change in blood sugar (%) |
|---|---|---|---|---|
| Group 1 | 20 | 23.1 ± 3.8 | 21.9 ± 3.3 | −5.19 |
| Group 2 | 20 | 22.9 ± 3.6 | 16.5 ± 4.1 | −27.95 |
| Group 3 | 20 | 22.4 ± 3.1 | 16.7 ± 2.6 | −25.45 |
| Group 4 | 20 | 22.6 ± 2.8 | 16.6 ± 3.4 | −26.55 |
| Group 5 | 20 | 22.5 ± 3.2 | 17.3 ± 2.6 | −23.11 |
| Group 6 | 20 | 22.7 ± 2.6 | 17.5 ± 3.2 | −22.91 |
| P value | | 0.045 | 0.047 | |

TABLE 10

Summary of the Effect of Xylooligosaccharides on Postprandial Blood Glucose in Hyperglycemic Mice of Example 6 of the Present Disclosure

| Groups | Number of animals | Blood glucose value (mmol/L) 0 hour | Blood glucose value (mmol/L) 2 hours | Change in blood sugar (%) |
|---|---|---|---|---|
| Group 1 | 20 | 21.9 ± 3.3 | 23.6 ± 3.2 | 7.76 |
| Group 2 | 20 | 16.5 ± 4.1 | 17.5 ± 3.7 | 6.06 |
| Group 3 | 20 | 16.7 ± 2.6 | 17.7 ± 2.5 | 5.99 |
| Group 4 | 20 | 16.6 ± 3.4 | 17.5 ± 2.8 | 5.42 |
| Group 5 | 20 | 17.3 ± 2.6 | 18.5 ± 2.6 | 6.94 |
| Group 6 | 20 | 17.5 ± 3.2 | 18.7 ± 3.2 | 6.86 |
| P value | | 0.047 | 0.043 | |

From Table 9 and Table 10, it can be found that the products prepared by the present disclosure can significantly reduce the blood glucose level of the mice, and the effects are superior to of the products prepared by the Comparative Examples.

From the above-mentioned Examples and Comparative Examples, it can be found that the present invention prepares a soluble dietary fiber with specific components by using continuous countercurrent leaching technology and continuous steaming technology processing in a transverse pipe and selecting a specific enzyme, has better effect on proliferation of *Bifidobacterium* and *Lactobacillus*, and can significantly reduce blood sugar The description of the above embodiments is only used to help to understand the method of the invention and its core idea. It should be noted that, various modifications and adaptations may also be made to the present disclosure by people having ordinary skill in the art without departing from the principles of the invention. These modifications and adaptations will also fall within the protection scope of the pending claims of the present disclosure.

The invention claimed is:

1. A preparation method of a soluble dietary fiber comprising:
    (A) subjecting lignocelluloses to continuous countercurrent leaching, separating and obtaining a solid material, specific operation of the continuous countercurrent leaching is: the lignocellulose raw material is pulverized into particles having a length or particle size of 0.1 cm to 5 cm, placed in a continuous countercurrent extractor, a solvent medium(s) is added in such an amount that the ratio of the raw material to the solvent medium is 1 g:(4-10) mL, the controlled temperature is 30° C. to 90° C., the extraction time is 20 to 60 minutes, then the solid material and the leach liquor which is rich in monosaccharides are separated by continuous solid-liquid separations;
    (B) subjecting the solid material obtained in step (A) to continuous steaming processing in a transverse pipe, obtaining a steamed material, the continuous steaming processing in a transverse pipe is: the solid material is pushed into a transverse pipe through a screw conveyor, a material plug is formed, steam is introduced, they are thoroughly mixed and steamed under the tumbling action of the screw conveying and the steam to efficiently dissolve the hemicellulose form the raw material; the steaming pressure is 0.2 to 1.0 MPa, and the steaming time is 10 to 90 minutes;
    (C) subjecting the steamed material obtained in step (B) to enzymolysis by xylanase, the steamed material is subjected to pressure relief and is sprayed into an enzymolysis tank, water is added to the enzymolysis tank, the mass ratio of material to water is adjusted to 1:(4-16), and the pH is adjusted to 3.5-6.5, xylanase is added for enzymolysis in an amount of $1\times10^4$ U to $8\times10^4$ U of xylanase per kilogram of dry matter, enzymolysis reaction is carried on to obtaining a soluble dietary fiber crude sugar liquor; the xylanase is a xylanase prepared by fermentation with a microbial strain or an endo-xylanase commercially available, the temperature of the enzymolysis reaction is 40° C. to 80° C., and the reaction time is 4 h to 20 h;
    (D) subjecting the crude sugar liquor obtained in step (C) to decolorization, desalination and filtration, obtaining a soluble dietary fiber sugar liquor; and
    (E) concentrating or drying, obtaining a soluble dietary fiber I;
    in the soluble dietary fiber I, the purity of xylooligosaccharides is 80% or more.

2. The preparation method according to claim 1, wherein after step (E), the method further comprises:
    (F) subjecting the soluble dietary fiber I prepared in step (E) to chromatographic separation, obtaining a soluble dietary fiber II and a raffinate;
    in the soluble dietary fiber II, the purity of the xylooligosaccharide is 90% or more.

3. The preparation method according to claim 2, wherein after step (F), the method further comprises:
    (G) compounding the raffinate obtained in step (F) with the soluble dietary fiber sugar liquor obtained in step (D), obtaining a soluble dietary fiber III;
    in the soluble dietary fiber III, a third purity of xylooligosaccharide is 70% or more.

* * * * *